US010980853B2

(12) United States Patent
Tsai et al.

(10) Patent No.: US 10,980,853 B2
(45) Date of Patent: Apr. 20, 2021

(54) PROCESS FOR PREPARING A CRASSOCEPHALUM CREPIDIOIDES EXTRACT, EXTRACT PREPARED THEREBY AND USE OF THE EXTRACT

(71) Applicants: DEVELOPMENT CENTER FOR BIOTECHNOLOGY, New Taipei (TW); DCB-USA LLC, Wilmington, DE (US)

(72) Inventors: Dai-Hua Tsai, Taipei (TW); Tzung Hsien Lai, Taipei (TW); Tsui Hsu Chan, New Taipei (TW); Yuh Shan Chung, New Taipei (TW); Li-Chuan Hsu, Taichung (TW)

(73) Assignee: DEVELOPMENT CENTER FOR BIOTECHNOLOGY, New Taipei (TW)

( * ) Notice: Subject to any disclaimer, the term of this patent is extended or adjusted under 35 U.S.C. 154(b) by 138 days.

(21) Appl. No.: 16/067,376

(22) PCT Filed: Dec. 31, 2015

(86) PCT No.: PCT/US2015/068337
§ 371 (c)(1),
(2) Date: Jun. 29, 2018

(87) PCT Pub. No.: WO2017/116476
PCT Pub. Date: Jul. 6, 2017

(65) Prior Publication Data
US 2019/0060382 A1 Feb. 28, 2019

(51) Int. Cl.
| A61K 36/28 | (2006.01) |
| A61K 36/00 | (2006.01) |
| A61K 31/513 | (2006.01) |
| A61K 45/06 | (2006.01) |
| A61K 31/704 | (2006.01) |
| A61P 35/00 | (2006.01) |
| A61K 9/14 | (2006.01) |

(52) U.S. Cl.
CPC .............. *A61K 36/28* (2013.01); *A61K 9/14* (2013.01); *A61K 31/513* (2013.01); *A61K 31/704* (2013.01); *A61K 45/06* (2013.01); *A61P 35/00* (2018.01); *A61K 2236/00* (2013.01); *A61K 2236/333* (2013.01); *A61K 2236/39* (2013.01); *A61K 2236/51* (2013.01); *A61K 2236/55* (2013.01)

(58) Field of Classification Search
None
See application file for complete search history.

(56) References Cited

U.S. PATENT DOCUMENTS

| 5,439,886 | A | * | 8/1995 | Ikeyama ............... C07K 14/47 435/7.2 |
| 5,776,727 | A | | 7/1998 | Ikeyama et al. |
| 7,223,423 | B2 | * | 5/2007 | Hwa ..................... A61K 8/97 424/725 |
| 8,034,589 | B2 | * | 10/2011 | Kosai ................... C07K 14/005 435/320.1 |
| 8,048,455 | B2 | | 11/2011 | Shyur et al. |
| 10,111,822 | B2 | * | 10/2018 | Shibuya ............... A61K 8/9711 |
| 2004/0013748 | A1 | | 1/2004 | Lee |
| 2005/0152867 | A1 | * | 7/2005 | Hwa ..................... A61K 8/97 424/74 |
| 2005/0221441 | A1 | * | 10/2005 | Nakamura ......... C07K 14/4753 435/69.4 |
| 2007/0036759 | A1 | | 2/2007 | Kosai et al. |
| 2008/0152737 | A1 | | 6/2008 | Shyur et al. |
| 2013/0281665 | A1 | | 10/2013 | Zhang et al. |
| 2014/0356301 | A1 | | 12/2014 | Shyur et al. |

FOREIGN PATENT DOCUMENTS

| CN | 101560304 B | 12/2011 |
| CN | 104208114 A | 12/2014 |
| JP | 2006199651 A | 8/2006 |
| JP | 2008105960 A | 5/2008 |
| JP | 2011195530 A | 10/2011 |
| TW | 201807033 A | 3/2018 |
| WO | 2008105436 | 9/2008 |

OTHER PUBLICATIONS

Machine English translation of JP2008105960.
Machine English translation of JP2006199651.
Machine English translation of JP2011195530.
Office Action issued by the German Patent Office dated Sep. 30, 2019 for the Germany counterpart Appln. No. 11 2015 007 252.7.
Michael V. Bell: Separations of Molecular Species of Phospholipids by High-Performance Liquid Chromatography: The Scottish Crop Research Institute, Invertgowrie, Dundee (DD2 5DA), Scotland: pp. 44-83.
Koh Tomimori, et al.: Antitumor activity and macrophage nitric oxide producing action of medicinal herb, Crassocephalum crepidiodes; BMC Complementary and Alternative Medicine 2012, 12:78: http://biomedcentral.com/1472-6882/12/78.
PCT/US2015/068337 International Search Report.
PCT/US2015/068337 Written Opinion.
Owokotomo, I. A. et al., International Journal of Chemistry, Apr. 2012, vol. 4, No. 2, pp. 34-37.

(Continued)

*Primary Examiner* — Michael Barker
*Assistant Examiner* — Randall O Winston
(74) *Attorney, Agent, or Firm* — Ladas & Parry LLP

(57) ABSTRACT

The present invention provides a process for the preparation of a *Crassocephalum crepidioides* extract, and the extract prepared thereby. The present invention further relates to a pharmaceutical composition/combination comprising the *Crassocephalum crepidioides* extract. The use of the extract and the composition/combination comprising the extract in the prevention or treatment of cancer is also provided.

33 Claims, 1 Drawing Sheet

(56) References Cited

OTHER PUBLICATIONS

Tomimori, Koh et al., BMC Complementary and Alternative Medicine, 2012, vol. 12, p. 78.
Written Opinion dated Feb. 3, 2020 by the Intellectual Property Office of Singapore.
I. A. Owokotomo, et al., International Journal of Chemistry, Apr. 2012, vol. 4, No. 2, pp. 34-37; and.
Koh Omimori, et al., BMC Complementary and Alternative Medicine, 2012, vol. 12, p. 78.
Office Action with a Search Report dated Nov. 3, 2020 for the China counterpart (PRC Pat. Appln. No. 201580085787.9) and an English Translation.
Editorial board of Lectures on Health: Heilongjiang Science and Technology Press, Harbin: The Latest Optimum Food and Medicine Bible: Jan. 1, 2013: 132-133.
Junying Hu: Radical Scavenging and Liver Protection Activities of *Crassocephalum crepidioides*): (World Phytomedicines): Issue 6: Nov. 30, 2005: 260-261.
Y. Asada, et al.: Pyrrolizidine Alkaloids from Crassocephalum crepidioides: Planta Medica: Dec. 31, 1985: vol. 51: Issue 6: 539-540.
Bukola C. Adedayo, et al: Blanching alters the phenolic constituents and in vitro antioxidant and anticholinesterases properties of fireweed (*Crassocephalum crepidioides*): Journal of Taibah University Medical Sciences: Dec. 24, 2015: vol. 10: Issue 4: 419-426.

* cited by examiner

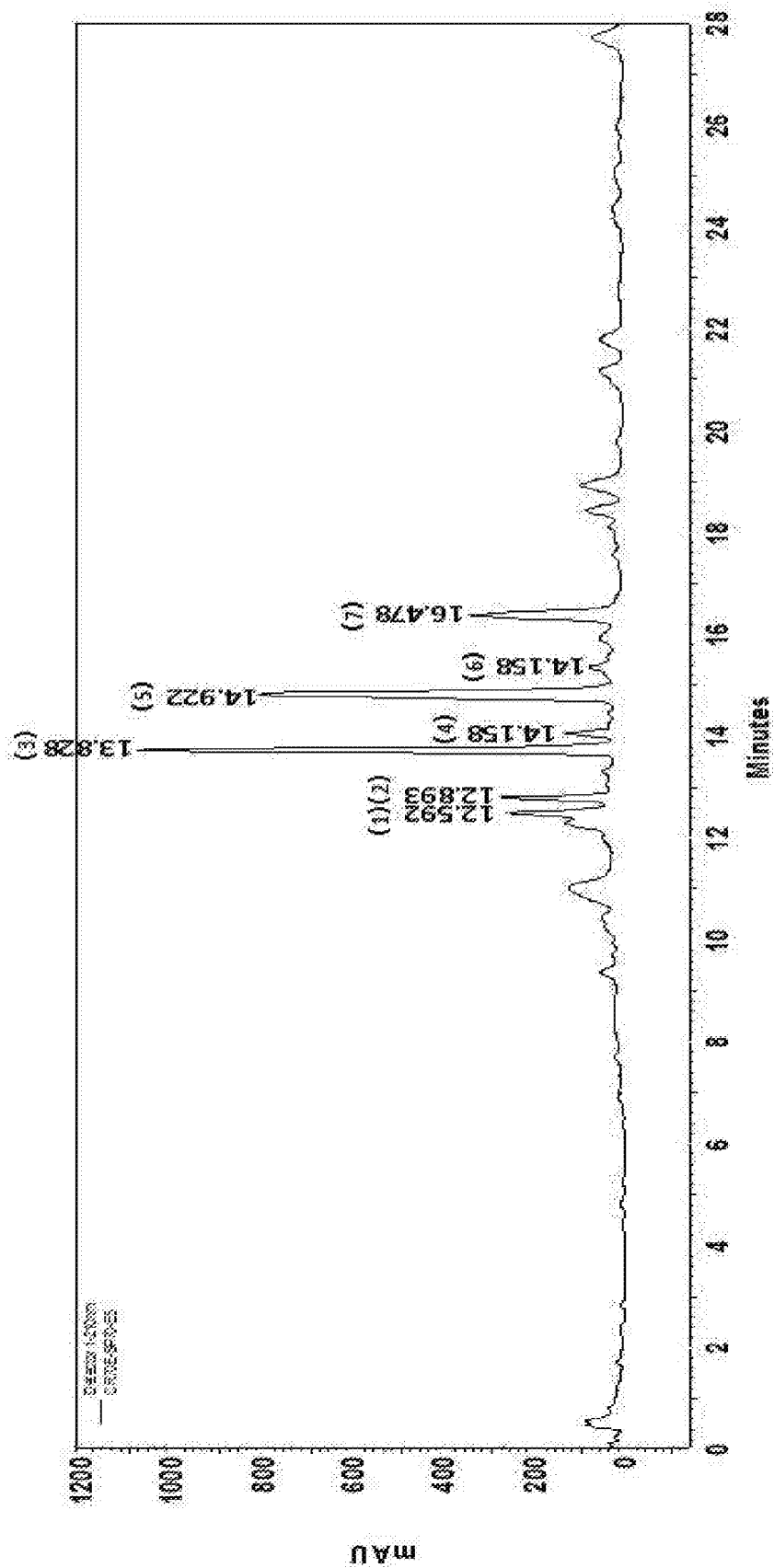

PROCESS FOR PREPARING A CRASSOCEPHALUM CREPIDIOIDES EXTRACT, EXTRACT PREPARED THEREBY AND USE OF THE EXTRACT

RELATED APPLICATION

This application is a national phase entry under 35 USC 371 of International Patent Application No.: PCT/US2015/068337 filed on 31 Dec. 2015, the entire contents of which is incorporated herein by reference.

FIELD OF THE INVENTION

The present invention relates to a process for the preparation of an herbal medicine extract of *Crassocephalum crepidioides*, and use of the *Crassocephalum crepidioides* extract in the treatment or prevention of cancer in a subject in need thereof.

BACKGROUND OF THE INVENTION

Cancer is a leading cause of death. Effective treatment has become a major focus of study in modern medicine, pharmaceuticals and academia. Conventional cancer treatments include surgery, chemotherapy and targeted therapy. Tumor tissue is first cut off by surgery. Remaining cells are then killed by chemotherapy and targeted therapy. However, such treatment program is far from sufficient for cancer patients at terminal stage. The survival rates and life quality of advanced cancer patients cannot be improved by conventional treatment methods.

Recently, it has been observed from clinical studies that the treatment effect on cancer patients receiving herbal medicine as adjuvant therapy (supportive therapy) has significantly improved, that herbal medicines can prevent or reduce toxic side effects of chemotherapy so as to improve the effect of chemotherapy, and that herbal medicines can enhance immune response of patients and shorten recovery time after surgery. Furthermore, it has been found that herbal medicines can be used alone to treat patients for whom surgery and/or chemotherapy are unsuitable.

*Crassocephalum crepidioides* is known as an edible plant traditionally used as an herbal medicine for treating inflammation diseases, hypertension, headache, vomiting, edema, constipation, etc.

Lie-fen Shyur et al. (U.S. Pat. No. 8,048,455 B2) discloses an extract of *Crassocephalum crepidioides* and found that the *Crassocephalum crepidioides* extract has a better effect in inhibiting the growth of melanoma cells in C57BL/6J mice than that of cisplatin (a chemotherapeutic agent). Lie-fen Shyur et al. also found that the active component contained in the *Crassocephalum crepidioides* extract is a galactolipid compound, named 1,2-di-O-α-linolenoyl-3-O-β-galactopyranosyl-sn-glycerol (dLGG), and that dLGG can inhibit the expression and production of iNOS, COX-2 and PEG2 in a macrophage cell line.

Lie-fen Shyur et al. (US 2014/356301 A1) further discloses a galactolipids-enriched plant extract, prepared by extracting a plant sample selected from a group consisting of *Gynura divaricata* subsp. *formosana* (Asteraceae), *Murdannia bracteata* (C. B. Clarke) J. K. Morton ex D. Y. Hong (Commelinaceae), and *Crassocephalum rabens* S. Moore (Asteraceae) with a series of solvents. This application also provides a composition for treating or preventing acute fluminant hepatitis and sepsis and related adaptations thereof, and for skin whitening, which comprises the plant extract or purified object thereof and a pharmaceutical, healthy or food acceptable vehicle.

Chien-Yung Lee (US 2004/0013748 A1) discloses an herbal combination for treating hepatoma and pancreatic cancer, which comprises Jiatonghao (*Crassocephalum crepidioides*), Fuling, etc.

YOKO ANIYA (WO 2008/105436 A1) discloses an extract from a plant naturally growing in Okinawa, i.e., *Crassocephalum crepidioides* S. Moore. YOKO ANIYA found that said extract can inhibit tumor necrosis factor-α and prostaglandin synthase-2.

The identification of new herbal extracts which can be used to treat cancers is needed.

SUMMARY OF THE INVENTION

In one aspect, the present invention relates to a process for preparing an extract of *Crassocephalum crepidioides*.

Another aspect of the present invention relates to the *Crassocephalum crepidioides* extract obtainable from the preparation process of the present invention.

Still another aspect of the present invention relates to a composition comprising the *Crassocephalum crepidioides* extract.

Still another aspect of the present invention relates to a combination comprising the *Crassocephalum crepidioides* extract and a chemotherapeutic agent.

A further aspect of the present invention is to provide a method for treating or preventing cancer of a subject in need comprising administering the *Crassocephalum crepidioides* extract of this invention alone or in combination with a chemotherapeutic agent to the subject. The present invention also provides the use of the *Crassocephalum crepidioides* extract or the composition/combination containing the extract in the treatment or prevention of cancer of a subject in need.

Other aspects and advantages of the invention will be apparent from the following description and the appended claims.

BRIEF DESCRIPTION OF THE DRAWINGS

FIG. 1 shows the HPLC pattern of the *Crassocephalum crepidioides* extract of the present invention.

DETAILED DESCRIPTION OF THE INVENTION

The present invention can be understood more readily by reference to the following detailed description of various embodiments of the invention, the examples, and the tables with their relevant descriptions. Unless otherwise defined, all terms (including technical and scientific terms) used herein have the same meaning as commonly understood by one of ordinary skill in the art to which this invention belongs. It will be further understood that terms such as those defined in commonly used dictionaries should be interpreted consistently with their meaning in the context of the relevant art and will not be interpreted in an idealized or overly formal sense unless expressly so defined herein. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±20%, preferably ±10%, more preferably ±5%, and even more preferably ±1%.

The Preparation Processes

The present invention provides a process for preparing an extract of *Crassocephalum crepidioides*, which comprises the steps of:
- (a) contacting *Crassocephalum crepidioides* plant with 70% ethanol to obtain a suspension;
- (b) separating the solid portion in the suspension from the liquid portion, and then collecting the liquid portion to obtain a crude extract;
- (c) diluting the crude extract to a 60% ethanol extract;
- (d) mixing the 60% ethanol extract with macroporous styrene-divinyl benzene resins;
- (e) pouring the 60% ethanol extract and macroporous resin mixture into a column;
- (d) washing the column with ethanol at a volume of about 2- to 10-fold to the volume of the column;
- (e) eluting the column with a solvent of ethanol/ethyl acetate or ethyl acetate and collecting the eluted fractions at different time intervals; and
- (f) analyzing each eluted fraction and determining which one is enriched in 1,2-di-O-α-linolenoyl-3-O-β-galactopyranosyl-sn-glycerol (dLGG) and contains phytol as the *Crassocephalum crepidioides* extract.

As used herein, the term "extract" refers to a concentrated preparation of the essential constituents of *Crassocephalum crepidioides* plant. The extract may be in the form of a liquid, extractum spissum, solid or powder.

As used herein, *Crassocephalum crepidioides* plant may be the whole plant or one or more parts thereof, including but not limited to, seeds, flowers, leaves, stems and roots. In an embodiment of the present invention, the *Crassocephalum crepidioides* plant is the whole plant. In another embodiment of the present invention, the *Crassocephalum crepidioides* plant is seeds, flowers, leaves, or any combination thereof. In a preferred embodiment of the present invention, the *Crassocephalum crepidioides* plant is dried and powdered.

In an embodiment of the present invention, in step (a), the ratio of the weight of the dried plant to the volume of the 70% ethanol solvent rages from about 1:1 to about 1:50, such as about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, or 1:50. In a preferred embodiment of the present invention, the ratio is about 1:1 to about 1:20. In a further preferred embodiment of the present invention, the ratio is about 1:10. Furthermore, the solid portion from step (b) can be subjected to the contacting conditions of step (a) to obtain a further suspension. Such repeating steps can be conducted one or more times, and all the crude extracts obtained therefrom are mixed together before conducting step (c).

In an embodiment of the present invention, the crude extract obtained from step (b) may be concentrated to an extractum spissum or a powder by any conventional concentration method for solutions, such as using a pressure-reducing rotary evaporator.

In an embodiment of the present invention, the 60% ethanol extract of step (c) may be obtained by directly diluting the crude extract with water. In a preferred embodiment of the present invention, the crude extract obtained from step (b) is concentrated to an extractum spissum, and then the extractum spissum is diluted in 60% ethanol to prepare the 60% ethanol extract of step (c).

According to the present invention, the macroporous styrene-divinyl benzene resin used therein is a styrene-divinycl benzene based resin, which has pores with an average pore radius ranging from about 45 Å to about 290 Å. The volume of the pores of the macroporous resin is about 1.5 ml/g, and the surface of the macroporous resin is an aromatic non-polar surface, and thus the surface is hydrophobic. In a preferred embodiment of the present invention, the macroporous resin is Sepabeads resin or Dialon resin. In a more preferred embodiment of the present invention, the macroporous resin is selected from, but not limited to, Sepabeads SP70 (Mitsubishi), Sepabeads SP710 (Mitsubishi), Sepabeads SP825 (Mitsubishi), Sepabeads SP850 (Mitsubishi), Sepabeads SP207 (Mitsubishi), Sepabeads SP700 (Mitsubishi), Dialon HP20 (Mitsubishi), MCI Gel CHP20P (Sigma-Aldrich), Amberlite® XAD®-2 (Sigma-Aldrich), and Amberlite® XAD®-4 (Sigma-Aldrich). In an even more preferred embodiment of the present invention, the macroporous resin is Sepabeads SP70, and the resin is pre-treated by 10% ethanol.

In step (d) of the preparation process of the present invention, the concentration of the ethanol used can be about 50%-90%, preferably about 70%-90%, and more preferably about 80%. The volume of the ethanol to wash the column is about 2- to 10-fold to the volume of the column, preferably about 4- to 8-fold, and more preferably about 4-fold.

In an embodiment of the preparation process of the present invention, the solvent used in step (e) is ethanol/ethyl acetate, wherein the volume ratio of ethanol to ethyl acetate ranges from about 1:1 to 1:50, preferably from about 1:1 to 1:30, more preferably from about 1:1 to 1:10, and even more preferably, is about 1:1. In another embodiment of the preparation process of the present invention, the solvent used in step (e) is ethyl acetate.

In step (f) of the preparation process of the present invention, the analysis method can be any method known to identify dLGG. For example, HPLC and HPLC-MS.

In a preferred embodiment of the present invention, the *Crassocephalum crepidioides* extract has 7 main peaks at the retention times of 12.59 min, 12.893 min, 13.828 min, 14.158 min, 14.922 min, 15.455 min, and 16.478 min, respectively, when determined by HPLC at the following conditions:

Column: Symmetry Shield C18, 15 μm, 4.6×150 mm

Temperature: ambient

Elution: $H_2O/CH_3CN$ gradient

Detection: UV 210 nm

| Time | Mobile phase (%) | |
|---|---|---|
| (min) | H$_2$O | CH$_3$CN |
| 0 | 35 | 65 |
| 10 | 3.5 | 96.5 |
| 20 | 3 | 97 |
| 22 | 0 | 100 |
| 27 | 0 | 100 |
| 28 | 35 | 65 |
| 35 | 35 | 65 |

Pharmaceutical Composition/Combination

The present invention provides a pharmaceutical composition comprising a therapeutically effective amount of a *Crassocephalum crepidioides* extract prepared by the preparation process of the present invention. The present invention also provides a pharmaceutical combination comprising a therapeutically effective amount of a *Crassocephalum crepidioides* extract prepared by the preparation process of the present invention and a therapeutically effective amount of a chemotherapeutic agent. The pharmaceutical composition/combination may include a pharmaceutically acceptable carrier or vehicle.

As used herein, the term "therapeutically effective amount" refers to a sufficient amount of an herbal extract or a compound being administered which will relieve to some extent one or more of the symptoms of the disease or condition being treated. The result can be reduction and/or alleviation of the signs, symptoms, or causes of a disease, or any other desired alteration of a biological system.

The term "chemotherapeutic agent" is used herein to refer to agents that have the functional property of inhibiting development or progression of a neoplasm in a human, particularly a malignant (cancerous) lesion, such as a carcinoma, sarcoma, lymphoma, or leukemia. Inhibition of metastasis or angiogenesis is frequently a property of chemotherapeutic agents. A chemotherapeutic agent may be a cytotoxic or cytostatic agent. The term "cytostatic agent" refers to an agent which inhibits or suppresses cell growth and/or multiplication of cells.

Non-limiting examples of chemotherapeutic agents include antimetabolites (e.g., azathioprine, 6-mercaptopurine, 6-thioguanine, fludarabine, pentostatin, cladribine, 5-fluorouracil (5FU), floxuridine (FUDR), cytosine arabinoside (cytarabine), methotrexate, trimethoprim, pyrimethamine, and pemetrexed); alkylating agents (e.g., cyclophosphamide, mechlorethamine, uramustine, melphalan, chlorambucil, thiotepa/chlorambucil, ifosfamide, carmustine, lomustine, streptozocin, busulfan, dibromomannitol, cisplatin, carboplatin, nedaplatin, oxaliplatin, satraplatin, triplatin tetranitrate, procarbazine, altretamine, dacarbazine, mitozolomide, and temozolomide); anthracyclines (e.g., daunorubicin, doxorubicin, epirubicin, idarubicin, and valrubicin); antibiotics (e.g., dactinomycin, bleomycin, mithramycin, anthramycin, streptozotocin, gramicidin D, mitomycins (e.g., mitomycin C), duocarmycins (e.g., CC-1065), and calicheamicins); antimitotic agents (including, e.g., maytansinoids, auristatins, dolastatins, cryptophycins, vinca alkaloids (e.g., vincristine, vinblastine, vindesine, vinorelbine), and taxanes (e.g., paclitaxel and docetaxel), and colchicines; topoisomerase inhibitors (e.g., irinotecan, topotecan, amsacrine, etoposide, teniposide, and mitoxantrone); and proteasome inhibitors (e.g., peptidyl boronic acids).

The composition/combination can be administered to a patient orally or parenterally in the conventional forms of preparations, such as capsules, microcapsules, tablets, granules, powder, troches, pills, suppositories, injections, suspensions and syrups. Suitable formulations can be prepared by methods commonly employed using conventional, organic or inorganic carriers, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfate, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol).

Utilities

The pharmaceutical composition/combination of the present invention can be used to treat or prevent cancer in a subject in need thereof.

As used herein, the terms "treat," "treating," and "treatment" refer to the administration of a therapeutically active agent, composition, drug, or combination to a subject that has a disease/disorder, or has a symptom of or a predisposition toward it, with the purpose to cure, heal, alleviate, relieve, alter, remedy, ameliorate, improve, affect or reduce the risk of the disorder, the symptoms of or the predisposition toward the disorder. For example, treating cancer refers to the treatment results in inhibition of cancer growth or cancer cell growth, regression in cancer growth (i.e. reducing the size of a detectable cancer), or the disappearance of a cancer.

As used herein, the term "subject" is intended to include mammals, primates, humans and non-human animals. For example, a subject can be a patient (e.g., a human patient or a veterinary patient), having a cancer. The term "non-human animals" of the invention includes all non-human vertebrates, e.g., non-human mammals and non-mammals, such as non-human primates, sheep, dog, cow, chickens, amphibians, reptiles, etc., unless otherwise noted.

The term "cancer" refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as that found in the breast, prostate, and colon, are known as adenocarcinomas. Malignant growths of connective tissue, e.g., muscle, cartilage, lymph tissue, and bone, are called sarcomas. Lymphomas and leukemias are malignancies arising among white blood cells.

In the context of neoplasm, cancer, tumor growth or tumor cell growth, inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention. In this context, the term "prevention" includes either preventing the onset of clinically evident neoplasia altogether or preventing the onset of a preclinically evident stage of neoplasia in individuals at risk. Also intended to be encompassed by this definition is the prevention of transformation into malignant cells or the arrest or reversal of progression of premalignant cells to malignant cells. This includes prophylactic treatment of those at risk of developing the neoplasia.

The following examples are provided to aid those skilled in the art in practicing the present invention. Even so, the examples should not be construed to unduly limit the present invention as modifications to and variations on the embodiments discussed herein may be made by those having ordinary skill in the art without departing from the spirit or scope of the present inventive discovery.

EXAMPLES

Example 1

Preparation of *Crassocephalum crepidioides* Extract 1.02 kg of dried *Crassocephalum crepidioides* (whole plant) was ground and dipped in a 70% ethanol solution having a volume 10-fold to the total weight of the dried plant for 24 hours, and then the plant extract was filtrated through NO. 1 filter under reduced pressure to obtain a first filtrate. The solid residue was further dipped in a 70% ethanol solution having a volume 5-fold to the total weight of the dried plant for 24 hours, and then the plant extract was filtrated through NO. 1 filter under reduced pressure to obtain a second filtrate. The first and second filtrates were mixed to obtain a *Crassocephalum crepidioides* crude extract, and the crude extract was concentrated under reduced pressure to obtain a 1.05-L extractum spissum of with a weight of 213.69 g, a concentration of 203.51 mg/mL, and a yield of 20.95%.

425 g of the extractum spissum was diluted with 12 L of 60% ethanol to obtain a raw extract. The raw extract was added to a container containing macroporous resin SP70 (Mitsubishi), which was pre-treated by 10% ethanol. The contents (including the resins and the diluted extract) in the container were stirred and then allowed to stand overnight. The contents were poured into a column. The elution rate of the column was controlled at 1.5- to 2-fold to the volume of the column per hour. The fraction firstly eluted was non-absorbed sample. The column was then eluted through a gradient way by the solvents of 80% ethanol and ethanol:ethyl acetate (1:1), respectively. The volume of each solvent was 4-fold to the volume of the column. The fraction eluted by ethanol:ethyl acetate (1:1) and enriched in dLGG was collected, and was concentrated and dried to obtain 45.82 g of dried product (Cr-E03) with a yield of 10.78%.

Example 2

Component Analysis of the *Crassocephalum crepidioides* Extract

Conditions for HPLC
Column: Symmetry Shield C18, 15 μm, 4.6×150 mm
Temperature: ambient
Elution: $H_2O/CH_3CN$ gradient
Detection: UV 210 nm

| Time (min) | Mobile phase (%) | |
|---|---|---|
| | $H_2O$ | $CH_3CN$ |
| 0 | 35 | 65 |
| 10 | 3.5 | 96.5 |
| 20 | 3 | 97 |
| 22 | 0 | 100 |
| 27 | 0 | 100 |
| 28 | 35 | 65 |
| 35 | 35 | 65 |

The spectrum of the *Crassocephalum crepidioides* extract (Cr-E03) is shown in FIG. 1. After comparison of Cr-E03 with standards and LCMS-APCI(+), it was confirmed that Peak (1) was dLGG ($[M^-H]^+$: 613, 595 and 335), and that Peak (2) was phytol (M.W.=296.5).

Example 3

Effects of *Crassocephalum crepidioides* Extract in the Inhibition of the Growth of MKN45 Cancer Cells MKN45 cells were incubated in RPMI-1640 medium (Sigma-Aldrich) containing 5% FBS (Gibco®). $6\times10^3$ cells were added to each well of a 96-well plate. Each well contained 180 μL of the above medium. The plate was incubated at 37° C. for 4 hours, and then 20 μL of various concentrations of each of the raw extract, Cr-E03 and dLGG were added to each well of the plate. Each concentration was tested with 3 replicates. After further incubation at 37° C. for 48 hours, the medium in the wells was removed, and 180 μL of 5% FBS medium containing 3-(4,5-dimethylthiazol-2-yl)-5-(3-carboxymethoxyphenyl)-2-(4-sulfophenyl)-2H-tetrazolium (MTS) were added to the wells. After reaction at 37° C. for 1 hour, the absorption values at 490 nm of the wells were measured by ELISA Reader (Model 680 Microplate Reader, Bio-Rad). $IC_{25}$, $IC_{50}$ and $IC_{75}$ values of the raw extract, Cr-E03 and dLGG, respectively, were obtained by calculation using GraphPad Prism 5 software (GraphPad Software, Inc). $IC_{25}$, $IC_{50}$ and $IC_{75}$ values are defined as the concentrations of the test sample which achieve 25%, 50% and 75%, respectively, of the maximal inhibition of the growth of MKN45 cells. The results are shown in Table 1.

TABLE 1

| Drug | $IC_{25}$(μg/mL) | $IC_{50}$(μg/mL) | $IC_{75}$(μg/mL) |
|---|---|---|---|
| Raw | 36.08 | 58.14 | 89.00 |
| Cr-E03 | 21.55 | 55.36 | 138.33 |
| dLGG | 35.86 | 47.31 | 61.96 |

As can be seen from Table 1, the raw extract, Cr-E03 and dLGG can all inhibit the growth of MKN45 cells.

Example 4

Effect of the Combination of *Crassocephalum crepidioides* Extract with 5-Fluorouracil (5-FU) or Epirubicin in the Inhibition of the Growth of MKN45 Cancer Cells Combinations of different concentrations of each of the raw extract, Cr-E03 and dLGG with different concentrations of each of 5-fluorouracil (5-FU) and epirubicin were prepared. The tests were conducted based on the same proceedings of Example 3, and the combination indexes (CI) of the combinations were also obtained by the calculation of GraphPad Prism 5 software. The results are shown in Table 2. CI theorem was first provided by Chou T. C. and Talalay P. in 1984 (Advances in Enzyme Regulation, 22:27-55, 1984). According to the CI theorem, CI=1 represents the combination having an addition/summation; CI<1 represents the combination having a synergism; and CI>1 represents the combination having an antagonism.

TABLE 2

| Tested Samples | Raw | | Cr-E03 | | dLGG | |
|---|---|---|---|---|---|---|
| Chemical Therapy Agents | 5FU | Epi | 5FU | Epi | 5FU | Epi |
| CI | 0.86 | 0.46 | 0.67 | 0.63 | 1.58 | 1.58 |

As shown in Table 2, both the raw extract and Cr-E03 can respectively combine with 5-FU or epirubicin and achieve a synergistic effect in the inhibition of the growth of MKN45 cells. However, no synergistic effect is observed from the combinations of dLGG with 5-FU and epirubicin, respectively.

Example 5

Effects of Cr-E03 and the Combination of Cr-E03 with 5-FU or Epirubicin in the Inhibition of the Growth of A549 Lung Cancer Cells and Colo205 Colon Cancer Cells The effects of Cr-E03 and the combination Cr-E03 with 5-FU or epirubicin in the inhibition of the growth of A549 and Colo205 cancer cell lines were determined based on methods similar to those of Examples 3 and 4.

It was found that Cr-E03 alone can effectively inhibit the growth of A549 cancer cell line with an $IC_{50}$ value of 75.6 μg/mL.

The inhibition effects of the combinations Cr-E03 with 5-FU and epirubicin, respectively, to the growth of A549 and Colo205 cell lines are shown in Table 3.

TABLE 3

| | Cell Lines | | | |
|---|---|---|---|---|
| | A549 | | Colo205 | |
| Chemical Therapy Agents | 5FU | Epi | 5FU | Epi |
| CI | 1.07 | 1.05 | 1.36 | 0.49 |

The results of Table 3 show that the combination of Cr-E03 with 5-FU or epirubicin can provide an additive effect in inhibition of A549 cells, and that the combination of Cr-E03 with epirubicin can provide a very strong synergistic effect in inhibition of Colo205 cells.

It should be understood that the above-mentioned detailed description and specific examples, while indicating preferred embodiments of the invention, are given by way of illustration only. Various changes and modifications within the spirit and scope of the invention will become apparent to those skilled in the art from this detailed description. All such modifications as would be obvious to one skilled in the art are intended to be included within the scope of the following claims.

What is claimed is:

1. A process for preparing an extract of *Crassocephalum crepidioides* comprising the steps of:
   (a) contacting a *Crassocephalum crepidioides* plant or part thereof with 70% ethanol to obtain a suspension comprising a solid portion and a liquid portion;
   (b) separating the solid portion in the suspension from the liquid portion, and then collecting the liquid portion to obtain a crude extract;
   (c) diluting the crude extract to a 60% ethanol extract;
   (d) mixing the 60% ethanol extract with macroporous styrene-divinyl benzene resins;
   (e) pouring the 60% ethanol extract and macroporous styrene-divinyl benzene resin mixture into a column;
   (f) washing the column with ethanol at a volume of about 2- to 10-fold to the volume of the column;
   (g) eluting the column with a solvent of ethanol/ethyl acetate or ethyl acetate and collecting the eluted fractions at different time intervals; and
   (h) analyzing each eluted fraction and recovering determining which one that is enriched in 1,2-di-O-α-linolenoy1-3-O-β-galactopyranosyl-sn-glycerol (dLGG) and contains phytol to obtain the *Crassocephalum crepidioides* extract.

2. The process according to claim 1, wherein the *Crassocephalum crepidioides* plant or part thereof is the whole plant.

3. The process according to claim 1, wherein the *Crassocephalum crepidioides* plant or part thereof is a plant part selected from the group consisting of seeds, flowers, leaves, and a combination thereof.

4. The process according to claim 1, wherein the *Crassocephalum crepidioides* plant or part thereof is dried and powdered.

5. The process according to claim 1, wherein the *Crassocephalum crepidioides* plant or part thereof is a dried plant and the ratio of the weight of the dried plant to the volume of the 70% ethanol in step (a) ranges from about 1:1 to about 1:50.

6. The process according to claim 5, wherein the ratio of the weight of the dried plant to the volume of the 70% ethanol in step (a) is about 1:10.

7. The process according to claim 1, wherein the macroporous styrene-divinyl benzene resin is selected from the group consisting of Sepabeads SP70 and Sepabeads SP710.

8. The process according to claim 1, wherein the macroporous styrene divinyl benzene resin is Sepabeads SP70.

9. The process according to claim 1, wherein the solvent in step (g) is ethanol/ethyl acetate, and wherein the volume ratio of ethanol to ethyl acetate is about 1:1.

10. The process according to claim 2, wherein the *Crassocephalum crepidioides* plant is dried and powdered.

11. The process according to claim 2, wherein the *Crassocephalum crepidioides* plant is a dried plant and the ratio of the weight of the dried plant to the volume of the 70% ethanol in step (a) ranges from about 1:1 to about 1:50.

12. The process according to claim 11, wherein the ratio of the weight of the dried plant to the volume of the 70% ethanol in step (a) is about 1:10.

13. The process according to claim 3, wherein the *Crassocephalum crepidioides* plant part is dried and powdered.

14. The process according to claim 13, wherein the *Crassocephalum crepidioides* plant part is a dried plant part and the ratio of the weight of the dried plant part to the volume of the 70% ethanol in step (a) ranges from about 1:1 to about 1:50.

15. The process according to claim 14, wherein the ratio of the weight of the dried plant part to the volume of the 70% ethanol solvent in step (a) is about 1:10.

16. A pharmaceutical composition comprising a therapeutically effective amount of the *Crassocephalum crepidioides* extract obtained by the process according to claim 1 and a pharmaceutically acceptable carrier, wherein the pharmaceutical composition is in a form selected from the group consisting of capsules, microcapsules, tablets, granules, troches, pills and suppositories.

17. A pharmaceutical combination comprising a therapeutically effective amount of the *Crassocephalum crepidioides* extract obtained by the process according to claim 1 and a chemotherapeutic agent, wherein the pharmaceutical composition is in a form selected from the group consisting of capsules, microcapsules, tablets, granules, powder, troches, pills and suppositories.

18. The pharmaceutical combination according to claim 17, wherein the chemotherapeutic agent is selected from the group consisting of an antimetabolite, an alkylating agent, an anthracycline, an antibiotic, an antimitotic agent, and a proteasome inhibitor.

19. The pharmaceutical combination according to claim 17, wherein the chemotherapeutic agent is 5-fluorouracil (5-FU) or epirubicin.

20. A pharmaceutical composition comprising a therapeutically effective amount of the *Crassocephalum crepidioides* extract obtained by the process according to claim 1 and a pharmaceutically acceptable carrier, wherein the pharmaceutical composition is in a form selected from the group consisting of capsules, microcapsules, tablets, granules, troches, pills and suppositories, and wherein the *Crassocephalum crepidioides* extract has 7 main peaks at retention times of 12.59 min, 12.893 min, 13.828 min, 14.158 min, 14.922 min, 15.455 min, and 16.478 min, respectively, when determined by HPLC at the following conditions:
Column: Symmetry Shield C18, 15 μm, 4.6×150 mm
Temperature: ambient
Elution: H$_2$O/CH$_3$CN gradient
Detection: UV 210 nm

| Time | Mobile phase (%) | |
|---|---|---|
| (min) | H$_2$O | CH$_3$CN |
| 0 | 35 | 65 |
| 10 | 3.5 | 96.5 |
| 20 | 3 | 97 |
| 22 | 0 | 100 |
| 27 | 0 | 100 |
| 28 | 35 | 65 |
| 35 | 35 | 65 |

21. A pharmaceutical combination comprising a therapeutically effective amount of the *Crassocephalum crepidioides* extract obtained by the process according to claim 1 and a chemotherapeutic agent, wherein the pharmaceutical composition is in a form selected from the group consisting of capsules, microcapsules, tablets, granules, troches, pills and suppositories, and wherein the *Crassocephalum crepidioides* extract has 7 main peaks at retention times of 12.59 min, 12.893 min, 13.828 min, 14.158 min, 14.922 min, 15.455 min, and 16.478 min, respectively, when determined by HPLC at the following conditions:
Column: Symmetry Shield C18, 15 μm, 4.6×150 mm
Temperature: ambient
Elution: H$_2$O/CH$_3$CN gradient
Detection: UV 210 nm

| Time | Mobile phase (%) | |
|---|---|---|
| (min) | H$_2$O | CH$_3$CN |
| 0 | 35 | 65 |
| 10 | 3.5 | 96.5 |
| 20 | 3 | 97 |
| 22 | 0 | 100 |
| 27 | 0 | 100 |
| 28 | 35 | 65 |
| 35 | 35 | 65. |

22. The pharmaceutical combination according to claim 21, wherein the chemotherapeutic agent is selected from the group consisting of an antimetabolite, an alkylating agent, an anthracycline, an antibiotic, an antimitotic agent, and a proteasome inhibitor.

23. The pharmaceutical combination according to claim 22, wherein the chemotherapeutic agent is 5-fluorouracil (5-FU) or epirubicin.

24. The pharmaceutical composition according to claim 16, which is in the form selected from the group consisting of capsules, microcapsules, tablets, troches, pills and suppositories.

25. The pharmaceutical composition according to claim 17, which is in the form selected from the group consisting of capsules, microcapsules, tablets, troches, pills and suppositories.

26. A method of treating cancer in a subject in need thereof which comprises administering to the subject a therapeutically effective amount of the *Crassocephalum crepidioides* extract obtained by the process according to claim 1.

27. A method of treating cancer in a subject in need thereof which comprises administering to the subject a therapeutically acceptable amount of the *Crassocephalum crepidioides* extract obtained by the process according to claim 1 in combination with a chemotherapeutic agent.

28. The method according to claim 27, wherein the chemotherapeutic agent is selected from the group consisting of an antimetabolite, an alkylating agent, an anthracycline, an antibiotic, an antimitotic agent, and a proteasome inhibitor.

29. The method according to claim 27, wherein the chemotherapeutic agent is 5-fluorouracil (5-FU) or epirubicin.

30. A method for treating cancer in a subject in need by administering to the subject a therapeutically effective amount of the *Crassocephalum crepidioides* extract obtained by the process according to claim 1, wherein the *Crassocephalum crepidioides* extract has 7 main peaks at retention times of 12.59 min, 12.893 min, 13.828 min, 14.158 min, 14.922 min, 15.455 min, and 16.478 min, respectively, when determined by HPLC at the following conditions:
Column: Symmetry Shield C18, 15 μm, 4.6×150 mm
Temperature: ambient
Elution: H$_2$O/CH$_3$CN gradient
Detection: UV 210 nm

| Time | Mobile phase (%) | |
|---|---|---|
| (min) | H$_2$O | CH$_3$CN |
| 0 | 35 | 65 |
| 10 | 3.5 | 96.5 |
| 20 | 3 | 21 |

-continued

| Time (min) | Mobile phase (%) | |
|---|---|---|
| | H$_2$O | CH$_3$CN |
| 22 | 0 | 100 |
| 27 | 0 | 100 |
| 28 | 35 | 65 |
| 35 | 35 | 65. |

31. A method for treating cancer in a subject in need by administering to the subject a therapeutically effective amount of the *Crassocephalum crepidioides* extract obtained by the process according to claim 1 in combination with a chemotherapeutic agent.

32. The method according to claim 31, wherein the chemotherapeutic agent is selected from the group consisting of an antimetabolite, an alkylating agent, an anthracycline, an antibiotic, an antimitotic agent, and a proteasome inhibitor.

33. The method according to claim 32, wherein the chemotherapeutic agent is 5-fluorouracil (5-FU) or epirubicin.

* * * * *